United States Patent [19]

Dunlap

[11] Patent Number: 4,507,113
[45] Date of Patent: Mar. 26, 1985

[54] HYPODERMIC JET INJECTOR

[75] Inventor: Kenneth W. Dunlap, Long Lake, Minn.

[73] Assignee: Derata Corporation, Minneapolis, Minn.

[21] Appl. No.: 444,048

[22] Filed: Nov. 22, 1982

[51] Int. Cl.³ .............................................. A61M 5/30
[52] U.S. Cl. ...................................... 604/71; 604/411
[58] Field of Search ................................. 604/68–72, 604/90, 405, 407, 411, 414, 246, 249; 215/149, 149.1, 149.9; 141/330, 329; 128/764

[56] References Cited

U.S. PATENT DOCUMENTS

| | | |
|---|---|---|
| 969,276 | 9/1910 | Harris . |
| 1,650,967 | 11/1927 | Smith . |
| 1,738,080 | 12/1929 | Smith . |
| 1,739,871 | 12/1929 | Smith . |
| 2,576,192 | 11/1951 | Poznik . |
| 2,594,040 | 4/1952 | Le Clair . |
| 3,330,276 | 7/1967 | Gordon . |
| 3,354,508 | 11/1967 | Draben ............................... 251/149 |
| 3,428,223 | 2/1969 | Lewiecki et al. . |
| 3,490,451 | 1/1970 | Yahner . |
| 3,521,633 | 7/1970 | Yahner . |
| 3,659,587 | 5/1972 | Baldwin ............................... 128/764 |
| 3,674,183 | 7/1972 | Venable et al. . |
| 3,779,371 | 12/1973 | Rovinski . |
| 3,783,895 | 1/1974 | Weichselbaum .................... 604/405 |
| 3,838,689 | 10/1974 | Cohen ................................. 604/90 |
| 3,908,651 | 9/1975 | Fudge ................................. 604/71 |
| 3,938,520 | 2/1976 | Scislowicz et al. ................. 604/405 |
| 4,059,107 | 11/1977 | Iriguchi et al. ..................... 604/71 |
| 4,148,420 | 4/1979 | Morrissette et al. . |
| 4,256,106 | 3/1981 | Shoor ................................. 604/411 |
| 4,314,658 | 2/1982 | Laauwe . |
| 4,338,933 | 7/1982 | Bayard et al. ...................... 604/411 |
| 4,387,879 | 6/1983 | Tauschinski ..................... 251/149.1 |
| 4,447,225 | 5/1984 | Taff et al. ............................ 604/71 |

Primary Examiner—C. Fred Rosenbaum
Assistant Examiner—Michelle N. Lester
Attorney, Agent, or Firm—Orrin M. Haugen; Thomas J. Nikolai; Douglas L. Tschida

[57] ABSTRACT

An improved hypodermic jet injector system in which specifically designed adapters are used for joining conventional medicament supply vials to the hypodermic jet injector during the filling of the medicament chamber thereof whereby the valving structure may be greatly simplified and the ready substitution of one medicament for another facilitated such that there is no need to purge the injector device of the previously used medicament. The adapter comprises a relatively low-cost attachment for a medicament supply vial including a stopper-piercing needle having both a liquid passage and an air passage therein. The adapter also includes a hollow recess of a predetermined shape which has a stretchable membrane forming one wall thereof, the membrane having a zero diameter hole formed through it when the membrane is unstretched. The liquid passage of the piercing needle leads to the hollow recess. When the adapter is coupled to the nose of the hypodermic jet injector device, the membrane is distended into the recess, thus opening the zero diameter hole in the membrane and allowing the medicament to flow from the vial, through the open hole in the membrane and into the medicament chamber of the injector device via its injection orifice.

9 Claims, 5 Drawing Figures

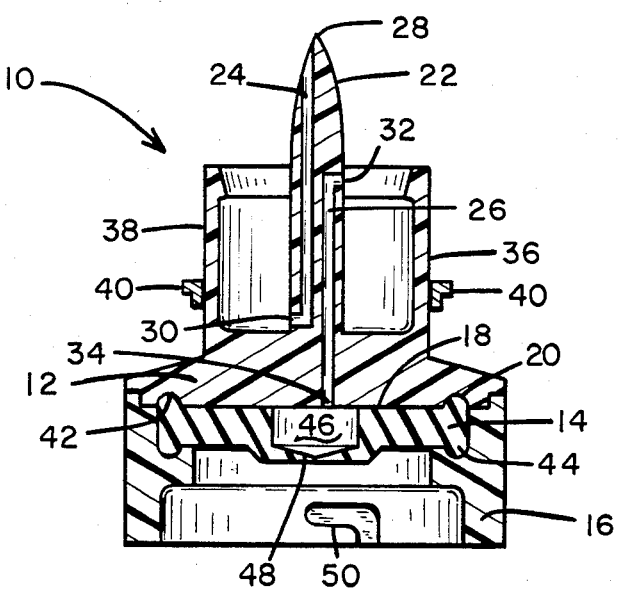
Fig. 1
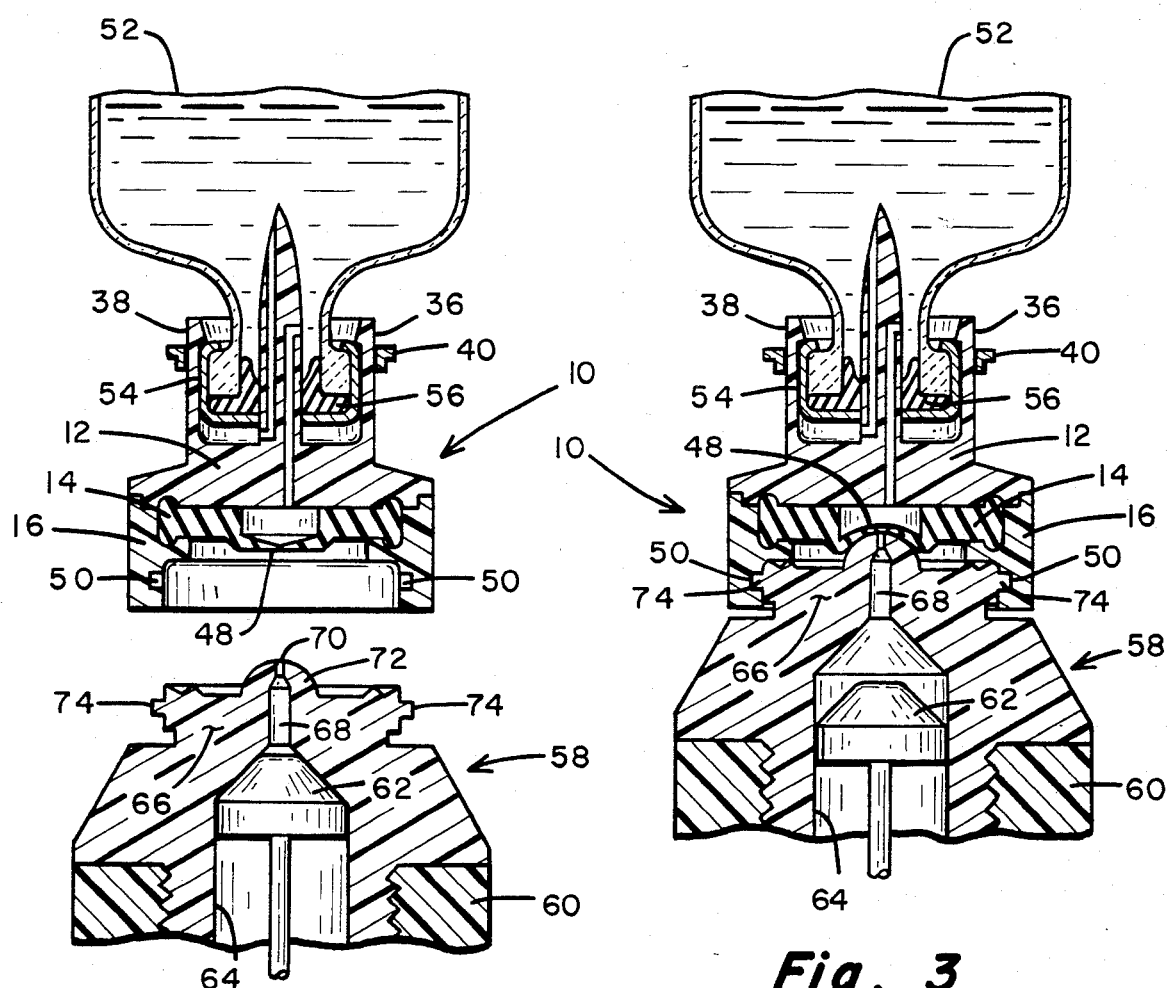
Fig. 2
Fig. 3

HYPODERMIC JET INJECTOR

BACKGROUND OF THE INVENTION

1. Field of the Invention

This invention relates generally to apparatus for facilitating the percutaneous administration of medicaments and more specifically to an improvement to a hypodermic jet injector device whereby its construction is simplified and its capability of use with different medicaments on an interchangeable basis is enhanced.

2. Discussion of the Prior Art

A need exists for a relatively painless way to administer drugs percutaneously. For example, persons afflicted with diabetes mellitus have a need to take one or more doses of insulin daily to maintain an appropriate glycemic balance. Because of the natural aversion to injecting oneself with a hypodermic needle, patient compliance with a physician's dosage regimen has been a continuing obstacle to the management of diabetes using insulin injections.

In the 1960's, there was introduced into the market a device called a hypodermic jet injector in which an adjustable, measured dose of a medicament could be administered in the form of a fine, high-velocity jet, delivered under sufficient force so as to pass through the skin tissue without requiring a hypodermic needle. The proper use of the jet injector proved to be a relatively painless, and therefore more acceptable, way of introducing medicaments into the body tissue. When used to inject insulin, it also afforded a further advantage in that the medicament was dispersed through a greater volume of subcutaneous tissue than occurs when a bolus injection of insulin is introduced through a conventional hypodermic needle. As such, the ability of the body to absorb the insulin was quicker and produced significantly less trauma to the tissue.

U.S. Pat. Nos. 3,330,276; 3,521,633 and 3,908,651 describe the construction and mode of operation of representative prior art hypodermic jet injector devices. Each discloses an arrangement in which a nozzle member is secured to the end of a injector body, the nozzle having a relatively small diameter orifice formed in the end thereof, the orifice communicating with a bore leading through a two-way valve member to a chamber. Disposed in the chamber is a piston which, when driven by power springs, moves through the medicament chamber to drive medicament through the bore and out of the orifice in the nozzle. Each of these patents also describes the valving structure whereby medicament may be withdrawn from a supply vial and through a series of bores and the two-way valve into the medicament chamber of the injector device. Thus, when the valve is in its "fill" position and the piston is retracted, the resulting vacuum created causes the medicament to be withdrawn from the vial and to flow through the series of bores and the valve so as to fill the medicament chamber. At the same time, the power springs are compressed. Next, the valve is rotated to establish a through-path from the medicament chamber to the nozzle orifice. When the device is triggered, the power springs rapidly drive the piston or plunger forward to force the medicament out of the chamber and through the orifice.

Because of the residual amount of medicament remaining in the various passages leading from the supply vial to the medicament chamber in these prior art devices, it is not a simple matter to substitute different medicament types by removing a first vial and replacing it with a vial containing a different medicament. For example, a physician may wish to prescribe an insulin injection regimen in which a long-lasting insulin such as Ultralente (trademark of Eli Lilly Company) is prescribed as a basal dose taken once daily and supplemented at mealtimes with a regular, fast acting insulin. With this substitution of insulin types, it is essential that the passageways and chamber of the injector be void of the first type at the time that the second type is to be drawn from its vial and into the chamber. With the type of injector described in the prior art, it was not uncommon that 12 units or more of insulin be entrained in the various bores and channels used to connect the supply vial to the injector chamber following the administering of a first injection. This residual amount effectively precluded the use of a prior art injector in a regimen where different types of insulin were to be administered.

The present invention is deemed to be an improvement over the prior art. Specifically, the use of the present invention reduces the residual amount of medicament remaining in the injector following an injection to negligible amounts. Furthermore, the adoption and use of the present invention materially simplifies the mechanical construction of the injector device. That is to say, by using the present invention, it is possible to eliminate the rotatable ball valve and its associated housing, thus reducing the cost of the device.

SUMMARY OF THE INVENTION

The hypodermic jet injector device shown in the prior art U.S. Pat. No. 3,908,651 to Fudge has been redesigned to completely eliminate the medicament vial holding device attached to the side of the jet injector body and the valving structure used to control the flow of medicament from the supply vial to the medicament chamber within the injector and the subsequent flow of the medicament from that chamber out through the orifice in the injection nozzle. This greatly simplifies the construction of the device.

In accordance with the teachings of the present invention, there is provided a low-cost, reusable adapter or coupling member for mating the medicament supply vial to the injection orifice formed through the nozzle. When filling the hypodermic jet injector device with medicament, the adapter with its associated supply vial is coupled to the nozzle portion of the injector device and, in doing so, an opening is created through a membrane seal member so that the medicament may be drawn through the injection orifice and into the medicament chamber as the device's piston is retracted. When giving an injection, the adapter along with its attached supply vial is removed from the nozzle of the injector gun causing the opening in the membrane seal to again close and prevent leaking from the vial. The user then positions the nozzle at the site on the skin where the injection is to be given and pushes the trigger button. The spring forces the piston rapidly through its chamber and the medicament is ejected out through the orifice.

Because of the manner in which the adapter member is constructed, air is effectively precluded from entering the chamber during the charging thereof. Furthermore, because of the dimensions involved, practically no medicament remains within the injector gun following the giving of an injection. As such, it is possible to immediately attach a second supply vial containing a different medicament to the ejector for filling its chamber with that different medicament without mixing that new charge with a residual quantity, as would be the case with the prior art.

Of course, if it is intended to inject a mixture of two or more different medicaments as a single dose, using the system of the present invention, a first supply vial having its own adapter may be coupled to the injector gun and a first quantity of medicament withdrawn therefrom into the medicament chamber. Next, a second supply vial having a different medicament and its own adapter may be coupled to the nozzle of the ejector gun and a predetermined quantity of that second medicament may be drawn into the chamber where it mixes with the first quantity with the mixture later being ejected as a single dose.

OBJECTS

It is thus a principal object of the present invention to provide an improved medicament injection device.

It is a further object of the present invention to provide a medicament injection device of simplified design when contrasted with the prior art.

It is another object of the present invention to provide a hypodermic jet injection device in which the medicament chamber of the device is filled by drawing the medicament through the same orifice from which it will later be ejected.

Yet another object of the present invention is to provide a hypodermic jet injection system which readily allows the substitution of different types of medicaments.

A yet further object of the invention is to provide a hypodermic jet injection system in which the medicament supply vial is equipped with an adapter for coupling the supply vial to the nozzle of the jet injector in such a fashion that no air is introduced into the medicament chamber as it is filled from the supply vial.

These and further objects and advantages of the present invention will become apparent from the following detailed description of an illustrative embodiment which is described in conjunction with the accompanying drawings.

DESCRIPTION OF THE DRAWINGS

FIG. 1 is a cross-sectional view illustrating the construction of the adapter unit forming a part of the present invention;

FIG. 2 is a cross-sectional view showing the adapter of FIG. 1 coupled to a medicament supply vial but not yet secured to the nozzle of the hypodermic jet injector;

FIG. 3 is a cross-sectional view showing the adapter and its associated vial coupled to the nozzle of the hypodermic jet injector;

DESCRIPTION OF THE PREFERRED EMBODIMENT

Figure 4:
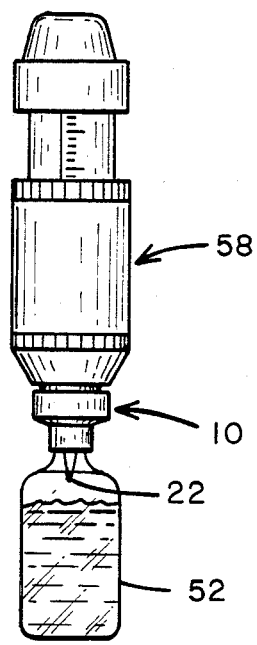
FIG. 4 shows the position of the assembly during a first stage of the filling operation.

Referring first to FIG. 1, there is illustrated by means of a cross-sectional view the internal construction of the adapter unit forming a part of the system of the present invention. It is indicated generally by numeral 10. As can be seen from this drawing, it is comprised basically of three parts, namely, a base portion 12, a diaphram-type seal 14, and a coupler ring 16. The base portion 12 is preferably formed from a sterilizable, non-toxic, plastic material, such as polysulfone, in an injection molding process. The base portion 12 includes a generally planar surface 18 having an annular groove 20 formed therein. Centrally located on the base portion 12 and extending outwardly from an opposed surface thereof is a needle member 22 which is adapted to pierce the conventional rubber stopper found in medicament vials where that medicament is to be administered by way of a subcutaneous injection. As is illustrated, first and second longitudinal bores 24 and 26 are formed through the needle portion 22. The bore 24 extends from a point proximate the tip or point of the needle 28 to a location near the base of the needle 30. The bore 26 extends between a transverse port 32 formed in the side wall of the needle and an exit point 34 which is generally centered in the circular surface 18.

Identified by numerals 36 and 38 are two of a plurality of fingers of a collet which is designed to fit about the neck of a conventional medicament vial. An and axially slideable ring 40 surrounds the collet portion of the adapter 10 and is used to compress the fingers, like fingers 36 and 38, to firmly grip the neck portion of the medicament vial.

The stretchable diaphram seal member 14 is preferably formed from natural rubber, is disc shaped and has an annular bead 42 cooperating with the annular recess 20 formed in the surface 18 of the base portion 10. Likewise, it has an annular bead 44 on the opposite surface of the disc which is adapted to mate with a corresponding annular groove or recess formed in the section 16. Thus, when the section 16 is bonded to the base portion 12, the rubber disc 14 is firmly gripped therebetween, with a liquid-tight seal resulting.

Formed at the center of the rubber disc 14 is a cylindrical recess or void 46. As can be seen, the bore 26 formed through the needle 22 communicates with that void 46. Integrally formed with the disc 14 and generally centrally located thereon is a diaphram segment 48 having a planar outer surface and a tapering inner surface extending from the side wall of the void 46 toward the geometric center of the disc.

During fabrication of the disc member 14, the disc is stretched in a suitable jig and while in its stretched condition, an aperture of a predetermined size is punched through the diaphram 48 at its center. Subsequently, when the stretching forces are removed, the aperture reduces to substantially a "zero diameter" hole proximate the center of the diaphragm member 48.

With no limitation intended, it has proved to be entirely suitable to have the diaphram portion of the disc 14 dimensioned such that at its center, it has a thickness in the range from about 0.002 to 0.015 inches and tapering to a thickness in the range of approximately 0.006 to 0.040 inches at its intersection with the cylindrical sidewalls of the depression or void 46. It is to be understood, however, that with natural rubbers of differing durometer values, different dimensions may be utilized.

The coupler ring 16 is generally cylindrical and is preferably fabricated from the same type of plastic used in forming the base member 12, polysofone being a non-toxic and FDA approved material which provides satisfactory performance. The inside diameter of the coupler ring 16 is dimensioned to fit about the nozzle member of the hypodermic jet injector and it includes two right-angle slots, as at 50, on diametrically opposed locations which are designed to mate with cylindrical bayonet pins which extend radially from the side surface of the injector's nozzle member to secure the adapter and its vial to the jet injector device during filling, as will subsequently be explained.

Referring to FIG. 2, there is shown a cross-sectional view with the adapter of FIG. 1 attached to the neck of a standard medicament vial 52 with the collet fingers 36 and 38 tightly gripping the metal cap portion 54 of the medicament vial. The needle element 22 of the adapter has been stabbed through the rubber plug 56 of the medicament vial 52 and it is assumed that the liquid medicament has flowed through the side port 32 in the needle and through the longitudinal bore 26 to fill the generally cylindrical void 46. It is to be noted that the point of exit 30 of the bore 24 is below the cap of the medicament vial and, as such, is exposed to the atmosphere. Thus, as the liquid medicament was made to flow from the vial to the recess or void 46, a volume of air was allowed to pass through the bore 24 to equalize the pressure within the vial, i.e., to maintain that pressure equal to atmospheric pressure. Because the diaphram 48 is in its relaxed, unstretched condition, the "zero diameter" hole therethrough is closed and no liquid flows through the membrane 48.

In FIG. 2 the adapter and associated medicament vial is poised above the nozzle of the hypodermic jet injector but, as yet, has not been mechanically coupled to it. Only a portion of the hypodermic jet injector is illustrated and it is identified generally by numeral 58. The body portion 60 thereof houses springs (not shown) arranged to drive a piston 62 within a cylinder 64. Threadedly secured to the head of the injector 58 is a nozzle member 66 having a tiny bore 68 formed therein, the bore terminating in a still finer orifice 70 formed in a hemispherically shaped protuberance or nose portion 72 of the nozzle member 66.

In the view of FIG. 3, the adapter 10 has been attached to the nozzle member 66 of the jet-injector device by fitting the bayonet pins 74 (FIG. 2) into the L-shaped slot 50 (FIG. 1) formed in the sidewall of the coupler ring 16 of the adapter. It can be seen that the rounded protuberance 72 of the nozzle has deflected the membrane 48 into the recess or void 46 of the sealing disc 44 and that this deflection has caused the membrane to stretch and thereby open the zero diameter hole formed through the membrane at its center. This now-opened hole is aligned with the orifice 70 and, as such, as the piston 62 is moved rearward in its cylinder relative to the nozzle, a vacuum is created in the cylinder which draws the medicament from the vial through the port 32 and the longitudinal bore 26. Because of the pressure equalizing bore 24, the volume of liquid removed from the vial is replaced with air.

When a predetermined measured dose has been drawn into the chamber of the jet injector, the adapter may again be removed from the nozzle of the jet injector and, in doing so, the membrane will seal itself to prevent any flow or leakage from the supply vial. The device is now ready to give an injection.

It is the essential that atmospheric pressure be maintained in the medicament reservoir to achieve the necessary accuracy of the dosage drawn and discharged by the jet injector. Pressure compensation using the system of the present invention requires that the technique described below be used.

Figure 5:
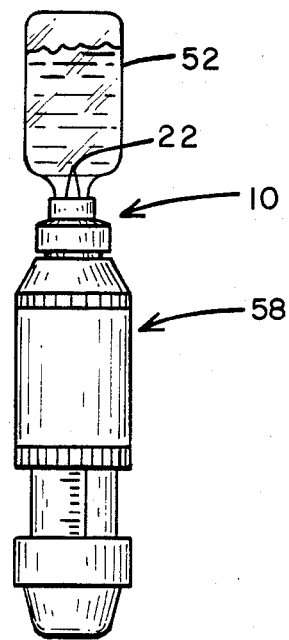
FIG. 5 illustrates the orientation of the device during a second state of the filling operation.

With reference to FIG. 4, the vial 52 and its attached adapter 10 are coupled to the jet injector device 58 in the manner already described, with the vial and the jet injector being in a generally vertical plane and the vial 52 being below the injector such that the medicament does not cover the needle. In this orientation, pressure due to the initial deflection of the membrane during coupling will be compensated for by air escaping out of the port 30. Next, the assembly is inverted as illustrated in FIG. 5 such that the needle 22 is submerged in the medicament. By waiting a brief period, e.g., approximately five seconds, with the assembly in the orientation of FIG. 5, the trapped air will rise above the medicament level in the vial. Now, a prescribed dosage can be drawn from the vial into the chamber of the jet injector. As the medicament is drawn in, air will replace the volume of the insulin drawn from the vial. That is, air will be drawn in through the port 30 and through the bore 24 and bubbles will be seen rising through the liquid. Keeping the assembly in the orientation shown in FIG. 5, the adapter may be twisted and removed from its bayonet coupling. Following removal medicament remains in the recess or void 46 and air will be excluded therefrom. Following removal, the vial assembly with its adapter may be stored in any attitude without spillage or seepage.

It can thus be seen that the present invention obviates the need to have a permanent attachment of the medicament vial to the jet injector as was the case with the prior art designs. Also, the valve arrangement for directing medicament from the vial to the jet injectors discharge chamber of the prior art has been eliminated. Furthermore, through the use of the present invention, an interchange of medicament types on a multi-daily basis or the intermixing of different medicament types for individual injections can be accommodated. For example, in the treatment of diabetes medical researchers have found that "intensified conventional therapy" (ICT) involving multi-daily injections has resulted in a reduction in long-term complications of the disease, e.g., blindness, renal failure, heart disease, limb loss, etc. The use of the present invention adds greatly to the flexibility in the use of variable types of insulins which are available in that sterile intermix can be maintained in actual daily practice of the ICT regimen.

The invention has been described herein in considerable detail, in order to comply with the Patent Statutes and to provide those skilled in the art with information needed to apply the novel principals, and to construct and use such specialized components as are required. However, it is to be understood that the invention can be carried out by specifically different equipment and devices, and that various modifications, both as to equipment details and operating procedures can be effected without departing from the scope of the invention itself.

What is claimed is:

1. In a hypodermic jet injector system including a hypodermic jet injector of the type having an injector body, an injector nozzle having an orifice therethrough and attachable on one end of said injector body, a medicament chamber within the injector body for receiving, via a delivery means, a predetermined measured quantity of medicament from a medicament supply vial and a means for forcibly ejecting said predetermined measured quantity of medicament through said orifice in said ejector nozzle, the improvement comprising:

(a) the delivery means comprises adapter means attachable to said medicament supply vial, said adapter means including:
  1. a base member;

2. a stretchable membrane abutting said base member and cooperating therewith to define a generally closed recess, said stretchable membrane having a zero diameter hole formed therethrough, said membrane being in sealing relation to said recess when said membrane is in its relaxed state;
3. probe means on said base member insertible into said supply vial for conveying liquid medicament from said supply vial to said recess; and (b) means on said injector nozzle for coupling said adapter means to said injector nozzle and distending said membrane from said relaxed state to open said zero diameter hole, said open hole being in general alignment with said orifice in said ejector nozzle for allowing flow of fluid from said recess through said orifice into said medicament chamber.

2. The improved hypodermic jet injector as in claim 1 wherein said adapter means further include means for maintaining atmospheric pressure within said supply vial as liquid medicament is conveyed to said recess and into said medicament chamber.

3. The improved hypodermic jet injector as in claim 1 wherein said ejector nozzle includes a protuberance surrounding said orifice, said protuberance having a shape corresponding to the shape configuration of said recess.

4. The improved hypodermic jet injector as in claim 1 and further including a collet member for receiving and gripping a neck portion of said medicament supply vial.

5. The improved hypodermic jet injector as in claim 2 wherein said probe means comprises a generally cylindrical needle member having a pointed end for piercing a cap portion of said vial, first and second longitudinal bores formed in said needle member and individually communicating with first and second ports formed in the sidewall of said needle member, said first longitudinal bore communicating with said recess and said second longitudinal bore communicating with the atmosphere.

6. The improved hypodermic jet injector as in claim 1 wherein said stretchable membrane is generally circular in its plan view and of a lesser thickness proximate said zero diameter hole than at its periphery.

7. The improved hypodermic jet injector as in claim 1 wherein said stretchable membrane is integrally formed at the center of an annular ring.

8. The improved hypodermic jet injector as in claim 7 wherein said stretchable membrane is formed from an elastomeric material.

9. The improved hypodermic jet injector as in claim 8 wherein said elastomeric material is rubber.

* * * * *